US008610765B2

(12) United States Patent
Yamaguchi

(10) Patent No.: US 8,610,765 B2
(45) Date of Patent: Dec. 17, 2013

(54) IMAGING APPARATUS, IMAGING METHOD, AND ENDOSCOPE APPARATUS

(75) Inventor: Shogo Yamaguchi, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 111 days.

(21) Appl. No.: 13/111,811

(22) Filed: May 19, 2011

(65) Prior Publication Data

US 2012/0127294 A1 May 24, 2012

(30) Foreign Application Priority Data

Nov. 24, 2010 (JP) ................................. 2010-261140

(51) Int. Cl.
*H04N 5/232* (2006.01)

(52) U.S. Cl.
USPC .......................................................... 348/73

(58) Field of Classification Search
USPC .......... 348/72, 73; 362/574; 396/17; 600/110
See application file for complete search history.

(56) References Cited

U.S. PATENT DOCUMENTS

| | | | |
|---|---|---|---|
| 6,975,641 B1 * | 12/2005 | Kurobe et al. ................ | 370/445 |
| 2004/0150724 A1 | 8/2004 | Nozaki et al. | |
| 2005/0239496 A1 * | 10/2005 | Sylvain ...................... | 455/552.1 |
| 2006/0092477 A1 | 5/2006 | Okado | |
| 2006/0293562 A1 * | 12/2006 | Uchimura et al. ............ | 600/110 |
| 2008/0139881 A1 * | 6/2008 | Cover et al. .................... | 600/103 |
| 2008/0262299 A1 | 10/2008 | Niida et al. | |
| 2009/0002547 A1 | 1/2009 | Endo et al. | |
| 2009/0076320 A1 | 3/2009 | Shigemori | |
| 2009/0247828 A1 * | 10/2009 | Watanabe et al. ............. | 600/131 |
| 2009/0284611 A1 | 11/2009 | Wood et al. | |
| 2010/0013657 A1 | 1/2010 | Ohta et al. | |
| 2010/0208850 A1 * | 8/2010 | Anderson et al. ............. | 375/340 |

FOREIGN PATENT DOCUMENTS

| | | |
|---|---|---|
| EP | 1 793 581 A1 | 12/2005 |
| EP | 1867280 | 12/2007 |
| JP | 9-305508 | 11/1997 |
| JP | 2001-028740 | 1/2001 |
| JP | 2001028740 A * | 1/2001 |
| JP | 2001-251335 | 9/2001 |
| JP | 2004-235787 | 8/2004 |
| JP | 2005-045458 | 2/2005 |
| JP | 2006-157851 | 6/2006 |
| JP | 2006-288543 | 10/2006 |
| JP | 2008-264252 | 11/2008 |
| JP | 2009-010749 | 1/2009 |

(Continued)

OTHER PUBLICATIONS

JP2009297187 Machine translation.*
JP2001028740 (A) Machine translation.*
Japanese Patent Application No. 2010-261140; Notice of Reasons for Rejection; Mailed Feb. 28, 2012 (English translation).
Japanese Patent Application No. 2010-261140, Notice of Reasons for Rejection, mailed Nov. 8, 2011, (with English Translation).

(Continued)

*Primary Examiner* — Mehrdad Dastouri
*Assistant Examiner* — Mohammed Rahaman
(74) *Attorney, Agent, or Firm* — Blakely, Sokoloff, Taylor & Zafman LLP

(57) ABSTRACT

A head separated type imaging apparatus includes a head unit and a main unit which are separated, the main unit processing an image signal transmitted from the head unit. The main unit includes a first communication unit transmitting/receiving data to/from the head unit via wireless communication, a second communication unit transmitting/receiving data to/from the head unit via wired communication, and a control unit detecting whether the second communication unit is communicable, and continuing, when the first and second communication units are switched based on a detection result therefrom, transmission/reception of the data which is performed before the switching.

18 Claims, 9 Drawing Sheets

(56) References Cited

FOREIGN PATENT DOCUMENTS

| | | | |
|---|---|---|---|
| JP | 2009-531873 | | 9/2009 |
| JP | 2009-247407 | | 10/2009 |
| JP | 2009-297187 | | 12/2009 |
| JP | 2009297187 A | * | 12/2009 |
| JP | 2010-025707 | | 2/2010 |
| JP | 2010-081975 | | 4/2010 |
| JP | 2010-094368 | | 4/2010 |

OTHER PUBLICATIONS

English Machine Translation of Japanese Patent Application No. 2009-297187.
Japanese Patent Application No. 2010-261140, Notice of Reasons for Rejection, mailed Feb. 28, 2012, (with English Translation).
English translation of JP-A 2001-028740 made by machine translator on JPO's web-site.
Japanese Patent Application No. 2012-100768, Notice of Reasons for Rejection, mailed May 6, 2012, (with English Translation).

* cited by examiner

IMAGING APPARATUS, IMAGING METHOD, AND ENDOSCOPE APPARATUS

CROSS-REFERENCE TO RELATED APPLICATION

This application is based upon and claims the benefit of priority from the prior Japanese Patent Application No. 2010-261140, filed on Nov. 24, 2010; the entire contents of which are incorporated herein by reference.

FIELD

Embodiments described herein relate generally to a head separated type imaging apparatus including a head unit and a main unit which are separated, the head unit imaging a subject and the main unit processing an image signal transmitted from the head unit, and to an imaging method and an endoscope apparatus.

BACKGROUND

Among conventional imaging apparatuses, there is one in which a camera device (head unit) including an image sensor (for example, a CCD (Charge Coupled Device) sensor, a CMOS (Complementary Metal Oxide Semiconductor) sensor, or the like) which images a subject is attached detachably to a host device (main unit). When the camera device is used in a state of being detached from the host device, the image signal of an image captured by the camera device is transmitted to the host device via wireless communication, and when the camera device is used in a state of being attached to the host device, the image signal of an image captured by the camera device is transmitted to the host device via wired communication.

DETAILED DESCRIPTION

An imaging apparatus according to an embodiment is a head separated type imaging apparatus including a head unit and a main unit which are separated, the main unit processing an image signal transmitted from the head unit. The main unit includes a first communication unit transmitting/receiving data to/from the head unit via wireless communication, a second communication unit transmitting/receiving data to/from the head unit via wired communication, and a control unit detecting whether the second communication unit is communicable, and continuing, when the first and second communication units are switched based on a detection result therefrom, transmission/reception of the data which is performed before the switching.

Hereinafter, embodiments of the present invention will be described in detail with reference to the drawings.
(First Embodiment)

In a first embodiment, the structure of a head separated type endoscope apparatus as an example of an imaging apparatus will be described. Further, an embodiment using CMOS (Complementary Metal Oxide Semiconductor) sensors as an image sensor (imaging device) will be described. However, any other sensor such as a CCD (Charge Coupled Device) sensor or the like may be used instead of the CMOS sensors.

Figure 1:
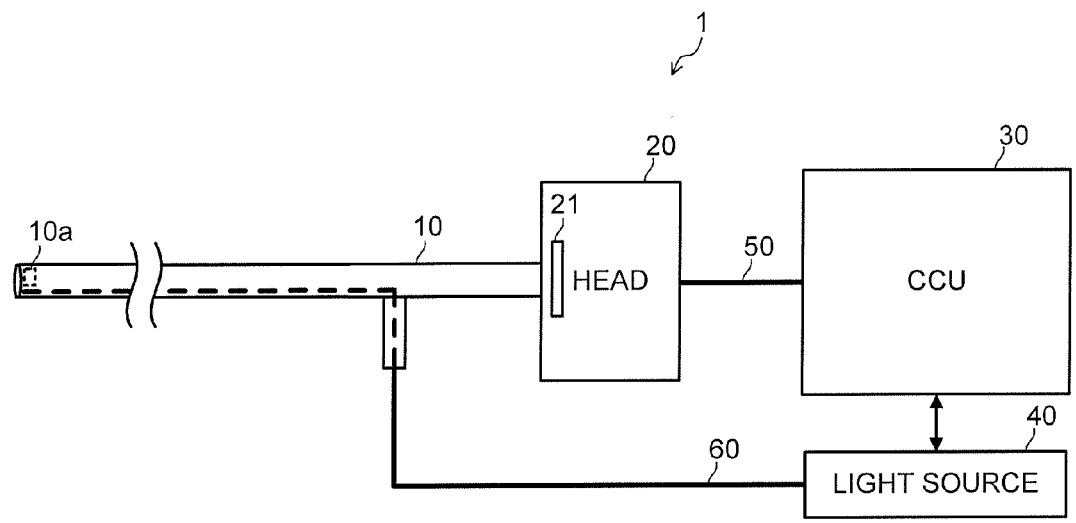
FIG. 1 is a structural diagram of an endoscope apparatus according to a first embodiment.

FIG. 1 is a structural diagram of an endoscope apparatus 1 according to the first embodiment. The endoscope apparatus 1 includes a scope 10 provided with an objective lens 10a on a leading end and inserted into a subject to be inspected, a head 20 transmitting via wireless communication or wired communication an image signal captured by an image sensor 21 (imaging unit) situated on an imaging plane of the objective lens 10a, a CCU (camera control unit) 30 processing the image signal transmitted from the head 20, a light source 40 for exposing an imaging area, and an optical fiber 60 for guiding the light from the light source 40 to a leading end portion of the scope 10. In addition, the scope 10 is attached detachably to the head 20. A camera cable 50 is a cable for wired communication between the head 20 and the CCU 30, and houses signal wires for transmitting/receiving correction data, an image signal, a control signal, and so on.
(Structure of the Head 20)

Figure 2:
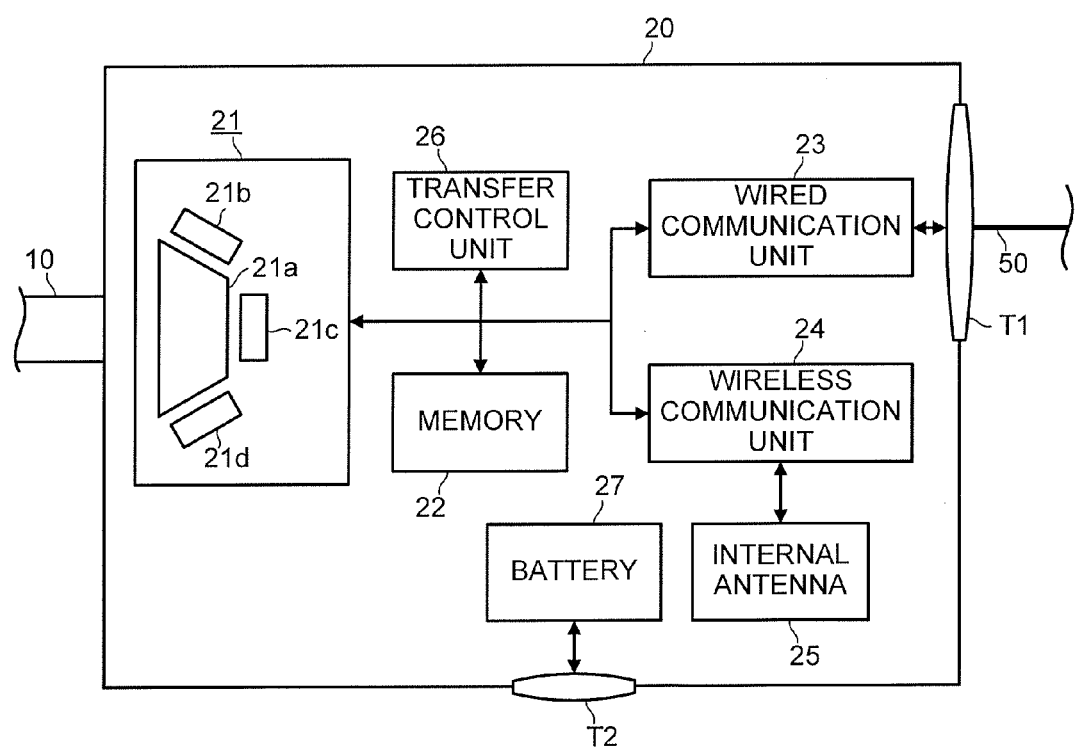
FIG. 2 is a structural diagram of a head.

FIG. 2 is a structural diagram of the head 20. The head 20 includes the image sensor 21, a memory 22, a wired communication unit 23, a wireless communication unit 24, an internal antenna 25, a transfer control unit 26, a battery 27, a connection terminal T1, and a charging terminal T2. The image sensor 21 is a three plate type image sensor, and is made up of a prism 21a separating the light from the objective lens 10a into three colors of R (red), G (Green), and B (Blue), and CMOS sensors 21b to 21d converting the light separated into the colors of R, G, B to electric signals. The three plate type image sensor has a characteristic in that it excels in color reproducibility because this sensor retains information of RGB for every pixel. The image sensor 21 is a color image sensor corresponding to full HD (high definition).

The image sensor 21 may be a single plate type instead of the three plate type. The single plate type image sensor has a color filter on each pixel of a CMOS sensor, and separates an electric signal outputted from the CMOS sensor into R, G, B signals in a circuit. This sensor has a characteristic in that it can be produced inexpensively because it is unnecessary to adhere the prism and the CMOS sensor to each other. In addition, examples of the array of color filters include color difference line sequential array and Bayer array. However, in the first embodiment it is not limited to the color difference line sequential array and Bayer array, and any one of various array types can be used.

The memory 22 is a non-volatile memory which is electrically rewritable (for example, a flash memory or the like) in which correction data (correction information) and setting conditions (for example, frame rate, gain, sensitivity, and so on) of the image sensor 21, ID (identifier), and so on are stored. In addition, for the memory storing the correction data, the setting conditions, and so on, any memory other than the flash memory may be used as long as it is rewritable.
(Correction Data)

In the image sensor 21, there exist two types of noise called fixed pattern noise (FPN) and random noise. In the first embodiment, correction data (correction information) of the fixed pattern noise are stored in advance in the memory 22 of the head 20. The correction data are transferred from the head 20 to the CCU 30 when the endoscope apparatus 1 is activated, and the image signal transmitted from the image sensor 21 is corrected using the transferred correction data.

Among the fixed pattern noise, there are base noise whose level (intensity) does not change due to external environment (for example, temperature and luminance) and defect noise (for example, white spot and black spot) whose level changes due to the external environment. In the memory 22, correction data for these two types of noise are stored. The respective correction data for the base noise and the defect noise will be described below.

(Correction Data for the Base Noise)

Figure 3:
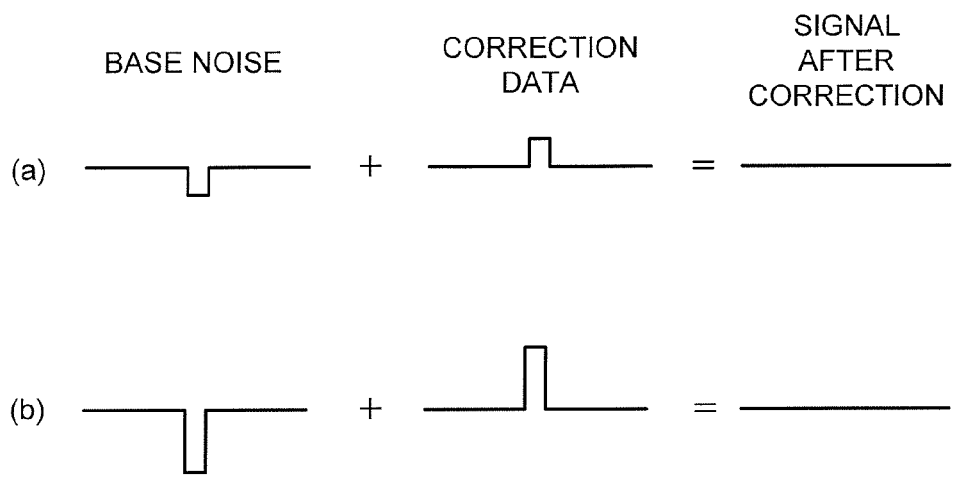
FIG. 3 is an explanatory diagram of correction data.

FIG. 3 is an explanatory diagram of correction data for the base noise. The base noise generates constant noise irrespective of the external environment. Accordingly, the base noise of the CMOS sensors provided in the image sensor 21 is measured in advance for every pixel, and correction data which cancel out the base noise as illustrated in FIG. 3 are stored for every pixel in the memory 22. The correction data of the base noise are stored in the memory 22 in the order of addresses of the pixels.

(Correction Data for Defective Pixels)

A white spot as defect noise refers to a pixel defect such that pixel data with values higher than those which should be originally outputted are outputted, and the pixel corresponding to the light receiving element thereof appears to be white, and occurs mainly due to a dark current. The dark current refers to a weak current which flows in the CMOS sensors even when no light is radiated, and occurs mainly due to a thermal factor or insulation failure. When the dark current is large, it causes noise in the image.

Further, a black spot as defect noise refers to a pixel defect such that pixel data with values lower than those which should be originally outputted are outputted, and the pixel corresponding to the light receiving element thereof appears to be black, and occurs mainly due to dust in the CMOS sensors. It is a failure which occurs when the dust blocks the light to be incident on pixels of the CMOS sensors or when circuits of the CMOS sensors are short circuited.

Figure 4:
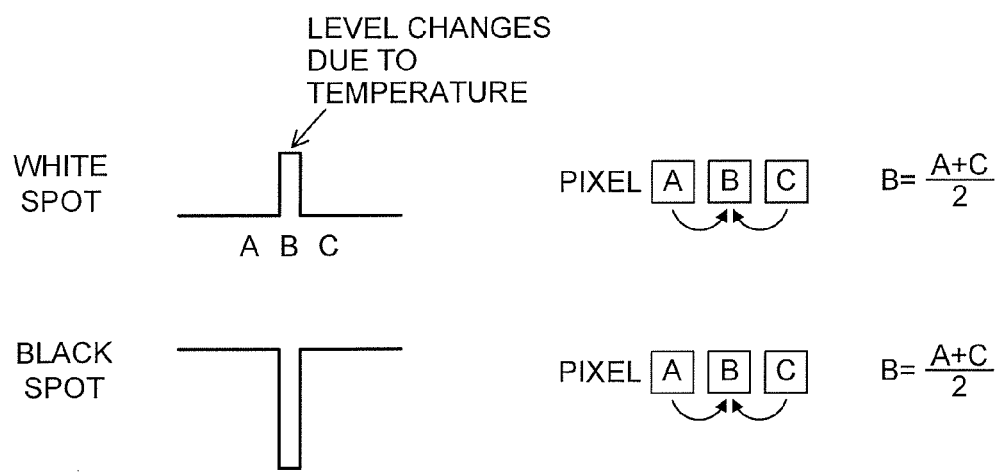
FIG. 4 is an explanatory diagram of a correcting method.

Among all the pixels of the CMOS sensors provided in the image sensor 21, addresses at which pixel defects such as white spot and black spot have occurred are stored in the memory 22 as correction data for defective pixels. FIG. 4 is an explanatory diagram of a method for correcting a defective pixel. As illustrated in FIG. 4, correction of defective pixels is performed such that image signals of both left and right adjacent pixels of a defective pixel are added and the added value is divided by two, and the resultant value is designated as an image signal of the defective pixel, thereby correcting the image signal of the defective pixel.

As described above, the following information is stored as the correction data in the memory 22. Further, when the correction data stored in this memory 22 are read, they are read in the order of 1→2→3.

1: The number of correction data.
2: Correction data (plural data) of base noise.
3: Correction data (plural data) of defective pixels.

Here, as the correction data of the base noise, correction data of respective pixels of the CMOS sensors of the image sensor 21 are stored together with addresses in the order of addresses of the pixels, and as the correction data of the defective pixels, addresses of the defective pixels are stored in the order of addresses of the pixels.

The wired communication unit 23 includes a serializer, an LVDS (low voltage differential signaling) conversion circuit, and so on, and transmits the correction data stored in the memory 22 and the image signal outputted from the image sensor 21 to the CCU 30 via the camera cable 50 connected to the connection terminal T1. Further, the communication unit receives initialization data (for example, resolution, clock, mode, and so on) transmitted from the CCU 30, which will be described later. In addition, the image signal is transmitted as a digital signal as it is to the CCU 30.

The wireless communication unit 24 transmits the correction data stored in the memory 22 and the image signal outputted from the image sensor 21 to the CCU 30 via the internal antenna 25. Further, the communication unit receives initialization data transmitted from the CCU 30, which will be described later. In addition, for the wireless communication, for example, methods defined by IEEE802.11a/b/g/n and Wireless HD can be used.

A transfer control unit 26 transfers the correction data and data of image signal, and the like to the CCU 30 based on an instruction from the CCU 30.

The battery 27 is a power source supplying power to respective circuits (image sensor 21, memory 22, wired communication unit 23, wireless communication unit 24, internal antenna 25, transfer control unit 26, and so on) provided in the head 20. The battery 27 is charged by an external power source (for example, a wall outlet) connected to the charging terminal T2. In addition, power lines for supplying power to the head 20 may be housed in the camera cable 50, and the battery 27 may be charged by power supplied via this camera cable 50.

(Structure of the CCU 30)

Figure 5:
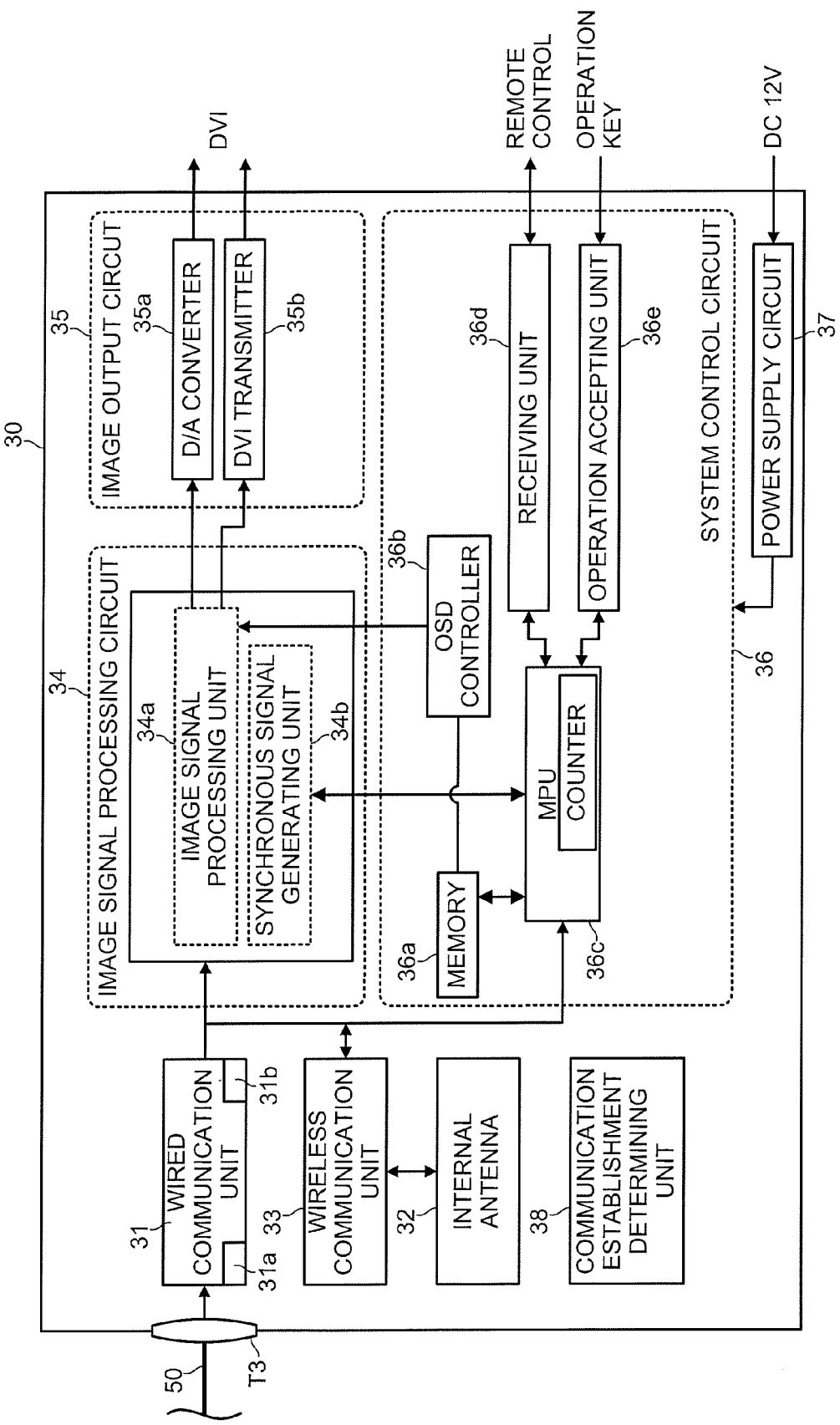
FIG. 5 is a structural diagram of a CCU.

FIG. 5 is a diagram illustrating the structure of the CCU 30. The CCU includes a connection terminal T3, a wired communication unit 31, an internal antenna 32, a wireless communication unit 33, an image signal processing circuit 34, an image output circuit 35, a system control circuit 36, a power supply circuit 37, and a communication establishment determining unit 38. To the connection terminal T3, the camera cable 50 is connected.

The wired communication unit 31 includes a deserializer 31*b* and an LVDS conversion circuit 31*b*. When power of the CCU 30 is turned on, the wired communication unit 31 starts establishing communication with the wired communication unit 23 of the head 20 and outputs, when the communication is established, the correction signal transmitted from the head 20 via the camera cable 50 to the system control circuit 36 and the image signal to the image signal processing circuit 34. Further, the wired communication unit 31 transmits a control signal and initialization data, which will be described later, outputted from the system control circuit 36 to the head 20 via the camera cable 50 connected to the connection terminal T3.

When power of the CCU 30 is turned on, the wireless communication unit 33 starts establishing communication with the wireless communication unit 24 of the head 20 and outputs, when the communication is established, the correction signal received via the internal antenna 32 to the system control circuit 36 and the image signal to the image signal processing circuit 34. Further, the wireless communication unit 33 transmits the control signal and initialization data outputted from the system control circuit 36 to the head 20 via the internal antenna 32. Here, when wireless communication is established, the wireless communication unit 33 transmits a signal periodically to the wireless communication unit 24 of the head 20, and maintains the state that the wireless communication with the wireless communication unit 24 is established.

The image signal processing circuit 34 includes an image signal processing unit 34a and a synchronous signal generating unit 34b. The image signal processing unit 34a processes the image signal outputted from the wired communication unit 31 and outputs the processed signal to the image output circuit 35. The image signal processing unit 34a sorts image signals outputted from the wired communication unit 31 in the order of the addresses of pixels, and thereafter corrects the image signals based on the correction data read from the memory 22 of the head 20 and stored in a memory 36a by an MPU 36c, which will be described later.

(Correction of the Base Noise)

The image signal processing unit 34a sorts the image signals in the order of addresses, and thereafter adds the correction data stored in the memory 36a to image signals having the same addresses, to thereby correct the image signals. The correction data stored in the memory 36a by the MPU 36c are created to cancel out the base noise of the CMOS sensors provided in the image sensor 21, and thus image signals can be corrected by adding the correction data to the image signals having the same addresses.

(Correction of the Defective Pixel Noise)

The image signal processing unit 34a recognizes an image signal of a defective pixel from the addresses of defective pixels stored in the memory 36a, adds image signals of both left and right adjacent pixels of this defective pixel and divides the added value by two, and designates the resultant value as the image signal of the defective pixel. The image signal of the defective pixel is corrected.

The image signal processing unit 34a performs enhancement processing such as de-mosaicking processing, knee correction, gamma correction, detail or matrix processing, or the like on the image signal after correction, and inputs the resultant signal to the image output circuit 35.

The synchronous signal generating unit 34b generates a synchronous signal used for imaging with the image sensor 21. The synchronous signal is generated at predetermined intervals corresponding to a set frame rate. The generated synchronous signal is outputted to the MPU 36c, and is transmitted from the wired communication unit 31 or the wireless communication unit 33 to the head 20.

The image output circuit 35 includes a D/A converter 35a and a DVI (digital visual interface) transmitter 35b, and outputs an image signal processed in the image signal processing circuit 34 to an external monitor (not illustrated) as an analog and digital RGB (red, green, blue) signals. In addition, the image output circuit may include an HD-SDI (high definition serial digital interface) transmitter or anHD-DVI (high definition digital visual interface) instead of the DVI transmitter 35b.

The system control circuit 36 includes the memory 36a, an OSD (on-screen display) controller 36b, the MPU (micro processing unit) 36c, a receiving unit 36d, and an operation accepting unit 36e, and controls the entire endoscope apparatus 1. The memory 36a is an EEPROM which is electrically rewritable. The memory 36a stores setting conditions (for example, exposure period, gain, and so on) of the CCU 30, initialization data of the head 20, and the number of initialization data (hereinafter referred to as initialization data number).

The exposure period is a parameter for adjusting the brightness of an image captured by the image sensor 21, and is equivalent to a shutter speed. As the exposure period, it will suffice to have a few types (for example, 1/240 seconds, 1/120 seconds, and the like). Setting of this exposure period can be changed through an external PC (personal computer) or operation keys, which will be described later.

For the memory storing these setting conditions, any memory other than the EEPROM may be used as long as it is rewritable. The OSD controller 36b displays text data, bit map, and/or the like in a superposed manner on the image of an image signal processed in the image signal processing unit 34a.

The MPU 36c controls the head 20, the CCU 30, and the light source 40 based on a remote control signal received in the receiving unit 36d, a processing content accepted in the operation accepting unit, and set information stored in the memory 36a.

(Transfer of the Correction Data)

Further, the MPU 36c specifies whether to transmit data via wired communication or via wireless communication, and instructs the transfer control unit 26 of the head 20 to transmit ID and correction data stored in the memory 22 of the head 20. The MPU 36c stores the ID and the correction data transmitted from the transfer control unit 26 of the head 20 in the memory 36a.

First, the MPU 36c instructs the transfer control unit 26 to transmit the ID stored in the memory 22 of the head 20, and stores the transmitted ID in the memory 36a. Then, the MPU 36c instructs the transfer control unit 26 to transmit the correction data number stored in the memory 22 of the head. 20, and stores the transmitted correction data number in the memory 36a.

Furthermore, the MPU 36c instructs the transfer control unit 26 to transmit the correction data of base noise and the address of a pixel from the memory 22 of the head 20, and stores the transmitted correction data of base noise and the transmitted address of a pixel in the memory 36a.

Next, the MPU 36c instructs the transfer control unit 26 to transmit correction data (address of a pixel) of a defective pixel from the memory 22 of the head 20, and stores the transmitted correction data of a defective pixel in the memory 36a of the CCU 30. The MPU 36c stores read-out correction data of pixel defect noise (addresses of defective pixels) in the order of reading them out, that is, the order of addresses.

Here, the MPU 36c increments the value of an internal counter every time the transmitted correction data are stored in the memory 36a, and at the point the value of this internal counter becomes equal to the correction data number in the memory 22, the MPU determines that reading of the correction data is finished and resets the value of the internal counter.

(Transfer of the Initialization Data)

The MPU 36c further transmits the initialization data stored in the memory 36a to the head 20 via the wired communication unit 31 or the wireless communication unit 33. The transmitted initialization data are stored in the memory 22 by the transfer control unit 26. Here, the MPU 36c increments the value of an internal counter every time the initialization data are read out and transmitted to the head 20, and at the point the value of this internal counter becomes equal to the initialization data number stored in the memory 36a, the MPU determines that transmission of the initialization data is finished and resets the value of the internal counter.

In addition, generally wired communication has a fast transmission speed and high stability of communication compared to wireless communication. Thus, the MPU 36c uses wired communication in priority when both wireless communication and wired communication are established.

The receiving unit 36d receives the control signal for remote control which is transmitted from an external PC or the like, and outputs the received signal to the MPU 36c. In addition, communication with the external PC is performed via an RS232-C serial port. The operation accepting unit 36e accepts processing operated by an external operation key, and outputs the accepted processing to the MPU 36c. Examples of the operation to be accepted by the operation accepting unit 36e include an operation about performing/not performing correction of an image signal (ON/OFF operation of correction), and an operation of a set value of gain.

The power supply circuit 37 converts externally supplied power into a predetermined voltage, and supplies the converted voltage to respective circuits in the CCU 30. Further, the power is also supplied to the head 20 via the camera cable 50 connected to the connection terminal T3.

The communication establishment determining unit 38 determines whether wired communication and wireless communication are established with the head 20 or not. Various methods can be used for determining this establishment of communication in the communication establishment determining unit 38. For example, in the first embodiment, LVDS is used when an image signal is transmitted via wired communication. In the LVDS the image signal is transmitted by differential signals, and thus it is possible to determine whether wired communication is established or not between the wired communication unit 31 and the wired communication unit 23 of the head 20 from the presence of voltage between two transmission paths.

Upon establishment of wired communication from a state that wired communication is not established, the communication establishment determining unit 38 outputs a "wired communication establishment signal" to the MPU 36c of the system control circuit 36. Further, when changing from the state that the wired communication is established to a state that the wired communication is not established, the communication establishment determining unit 38 outputs a "wired communication disconnection signal" to the MPU 36c of the system control circuit 36.

Further, when establishment of communication in wireless communication is to be determined, for example, data transmission for confirming connection defined by IEEE802.11a/b/g/n or Wireless HD is performed, and then whether wireless communication is established or not between the wireless communication unit 33 and the wireless communication unit 24 of the head 20 can be determined by whether there are response data (Ack) from the wireless communication unit 24 of the head 20 or not.

Upon establishment of wireless communication from a state that wireless communication is not established, the communication establishment determining unit 38 outputs a "wireless communication establishment signal" to the MPU 36c of the system control circuit 36. Further, when changing from the state that the wireless communication is established to a state that the wireless communication is not established, the communication establishment determining unit 38 outputs a "wireless communication disconnection signal" to the MPU 36c of the system control circuit 36.

The light source 40 includes a lamp and a lens. Further, the optical fiber 60 is connected to the light source 40. The lamp is, for example, a xenon lamp and emits light for exposing the imaging area of the image sensor 21. The lens guides the light emitted from the lamp into the optical fiber 60. The light guided into the optical fiber 60 is led to the leading end portion of the scope 10 for exposing the imaging area of the image sensor 21.

(Operation of the Endoscope Apparatus 1 when Activated)

Figure 6:
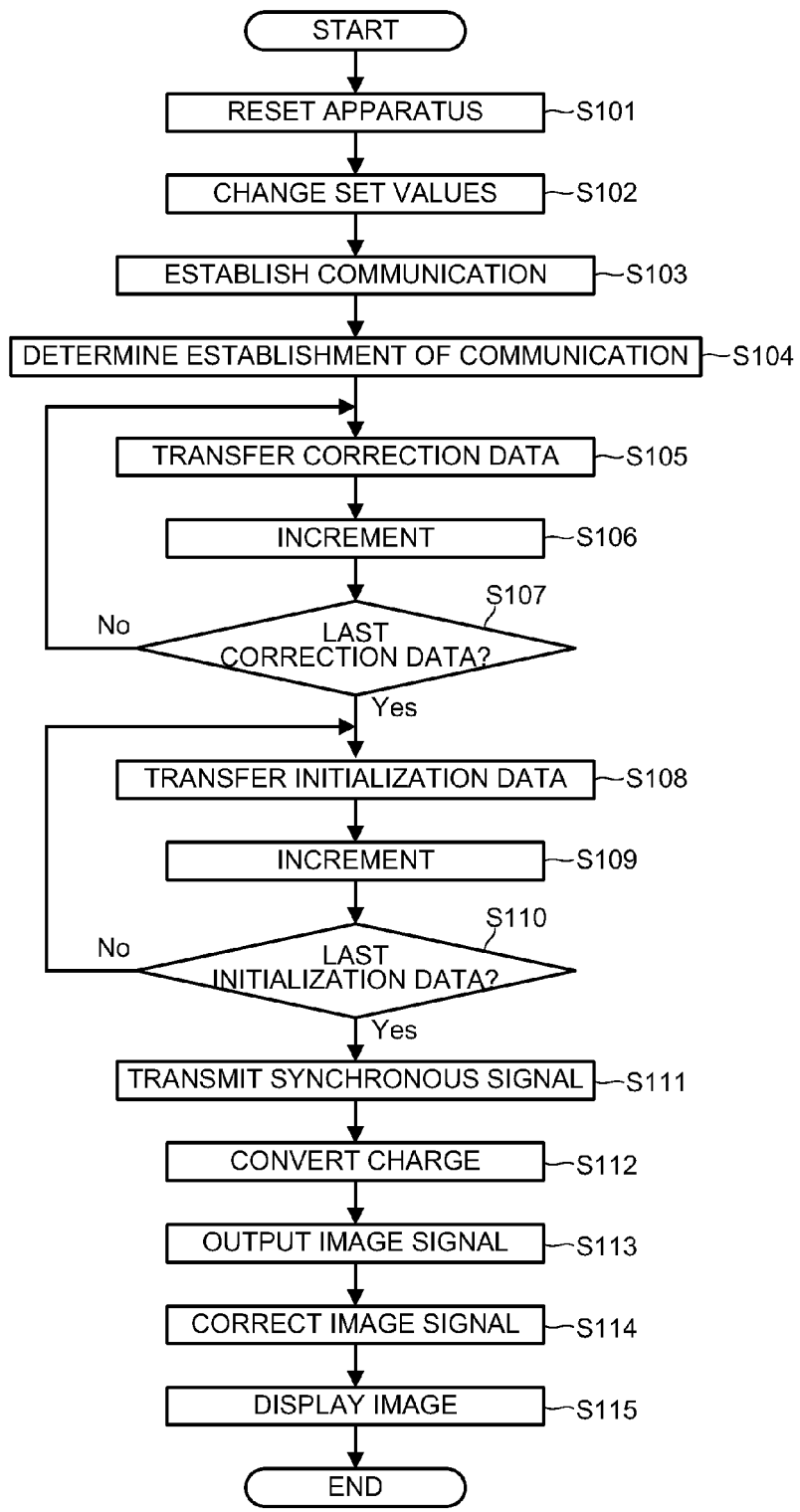
FIG. 6 is a flowchart illustrating operation of the endoscope apparatus.

FIG. 6 is a flowchart illustrating operation of the endoscope apparatus 1 according to the first embodiment. Hereinafter, the operation of the endoscope apparatus 1 according to the first embodiment will be described with reference to FIG. 6. Note that in the following description, the operation of the endoscope apparatus 1 will be described taking an example that one of wired communication and wireless communication is established. Further, in FIG. 6, the initialization data are transferred after transferring the correction data, but the correction data may be transferred after the initialization data are transferred.

(Step S101)

When power of the CCU 30 is turned on, the MPU 36c resets the image signal processing circuit 34 and the image output circuit 35. The reset mentioned here is, specifically, initialization of image processing setting. Further, the light source 40 turns on the lamp based on a control signal from the MPU 36c. The light from the lamp is guided into the optical fiber 60 and is radiated via the leading end portion of the scope 10 for exposing the imaging area of the image sensor 21.

(Step S102)

The MPU 36c reads out the setting conditions (for example, exposure period, gain, and so on) of the CCU 30 from the memory 36a, and changes the set values of the image signal processing circuit 34 and the image output circuit 35 to the values read from the memory 36a.

(Step S103)

The wired communication unit 31 of the CCU 30 starts communication with the wired communication unit 23 of the head 20. Further, the wireless communication unit 33 of the CCU 30 starts communication with the wireless communication unit 24 of the head 20. The communication establishment determining unit 38 outputs the "wired communication establishment signal" when the communication between the wired communication unit 31 of the CCU 30 and the wired communication unit 23 of the head 20 is established. Further, the communication establishment determining unit 38 outputs the "wireless communication establishment signal" when the communication between the wireless communication unit 33 of the CCU 30 and the wireless communication unit 24 of the head 20 is established.

(Step S104)

The MPU 36c determines which of wired communication and wireless communication is established based on the "wired communication establishment signal" or the "wireless communication establishment signal" outputted from the communication establishment determining unit 38.

(Step S105)

The MPU 36c starts obtaining the correction data from the memory 22 of the head 20 when the "wired communication establishment signal" or the "wireless communication establishment signal" is outputted from the communication establishment determining unit 38. At this time, when the "wired communication establishment signal" is outputted from the communication establishment determining unit 38, the MPU 36c instructs the transfer control unit 26 to transmit the correction data from the memory 22 of the head 20 via wired communication. On the other hand, when the "wireless communication establishment signal" is outputted from the communication establishment determining unit 38, the MPU 36c instructs the transfer control unit 26 to transmit the correction data from the memory 22 of the head 20 via wireless communication.

(Step S106)

First, the MPU 36c instructs the transfer control unit 26 to transmit the ID and the correction data number, and stores the transmitted ID and correction data number in the memory 36a. Next, the MPU 36c instructs the transfer control unit 26 to sequentially transmit the correction data, and stores the transmitted correction data in the memory 36a. At this time, the MPU 36c increments the value of the internal counter every time a piece of the correction data is stored in the memory 22.

(Step S107)

The MPU 36c determines whether the piece of the correction data stored in step S106 is the last piece of the correction data or not. Specifically, the MPU 36c determines whether or not the value of the internal counter is equal to the correction data number stored in the memory 36a.

When the value of the internal counter is not equal to the correction data number stored in the memory 36a (No in Step S107), the MPU 36c repeats the operation of step S105 to step S107 until the value of the internal counter becomes equal to the correction data number stored in the memory 36a.

(Step S108)

When the value of the internal counter is equal to the correction data number stored in the memory 36a (Yes in Step S107), the MPU 36c reads out the initialization data (for example, resolution, clock, mode, and so on) from the memory 36a and transmits the read data to the head 20. The initialization data transmitted to the head 20 are stored in the memory 22 by the transfer control unit 26.

(Step S109)

The MPU 36c increments the value of the internal counter every time a piece of the initialization data is transferred.

(Step S110)

The MPU 36c determines whether the piece of the initialization data transferred in the step S108 is the last piece of the initialization data or not. Specifically, the MPU 36c determines whether or not the value of the internal counter is equal to the initialization data number stored in the memory 36a.

When the value of the internal counter is not equal to the initialization data number stored in the memory 36a (No in Step S110), the MPU 36c repeats the operation of step S108 to step S110 until the value of the internal counter becomes equal to the initialization data number stored in the memory 36a.

When the value of the internal counter is equal to the initialization data number stored in the memory 36a (Yes in Step S110), the MPU 36c proceeds to the next step.

(Step S111)

The synchronous signal generating unit 34b generates a synchronous signal and transmits the generated synchronous signal to the head 20 at predetermined time intervals.

(Step S112)

Upon reception of the synchronous signal transmitted from the synchronous signal generating unit 34b, the image sensor 21 accumulates a charge in a phototransistor for every scanning line, converts the accumulated charges in respective phototransistors into voltages, and amplifies and reads out the voltages.

(Step S113)

The charges accumulated in the respective phototransistors of the image sensor 21 are converted into voltages for every scanning line, and thereafter amplified, read out, and transmitted to the CCU 30 as an image signal.

(Step S114)

The image signal processing unit 34a of the image signal processing circuit 34 performs sorting of pixel information in the image signal transmitted from the head 20, and performs correction on this sorted image signal. The image signal processing unit 34a corrects the image signal based on the correction data stored in the memory 36a. Furthermore, the image signal processing unit 34a performs enhancement processing and/or the like on the image signal after correction, and then outputs the processed image signal to the image output circuit 35.

(Step S115)

The image output circuit 35 outputs the image signal outputted from the image signal processing unit 34a to an external monitor (not illustrated) as an analog and digital RGB (red, green, blue) signals, and a corrected image is displayed on this monitor.

(Operation of the Endoscope Apparatus 1 when Transferring Data)

Next, operation of the endoscope apparatus 1 when transferring data according to the first embodiment will be described with respect to the following three cases.

Case 1: Wireless communication is established, and then wired communication is established.

Case 2: Wired communication is established, and then wireless communication is established.

Case 3: Wired communication is established and then wireless communication is established, and thereafter the wired communication is disconnected.

(Case 1)

The case 1 will be described. As the situation that wireless communication is established and then wired communication is established, for example, it is conceivable that the endoscope apparatus 1 is activated in a state that the camera cable 50 is removed, and thereafter the head 20 and the CCU 30 are connected by the camera cable 50.

When wireless communication is established first in step S103 of FIG. 6, the communication establishment determining unit 38 outputs the "wireless communication establishment signal". The MPU 36c determines that wireless communication is established based on the "wireless communication establishment signal" outputted from the communication establishment determining unit 38, and instructs the transfer control unit 26 to transmit the ID and the correction data via wireless communication.

When wired communication is established and the communication establishment determining unit 38 outputs the "wired communication establishment signal" while the ID and the correction data are obtained via wireless communication, the MPU 36c determines that wired communication is established based on the "wired communication establishment signal" outputted from the communication establishment determining unit 38, and instructs the transfer control unit 26 to switch the communication with the head 20 from wireless communication to wired communication.

The MPU 36c instructs the transfer control unit 26 to transmit the ID via wired communication. The MPU 36c determines whether the ID transmitted from the transfer control unit 26 and the ID obtained when the wired communication is established are the same or not. When the IDs are the same, the MPU 36c determines to what point the correction data have been transferred from the value of the internal counter, and instructs the transfer control unit 26 to transfer the rest of the correction data via wired communication. Further, when the IDs are not the same, the MPU 36c resets the value of the internal counter, and instructs the transfer control unit 26 to transfer the correction data from the beginning.

Although the operation when the correction data are transferred has been described above, note that operation when the initialization data and the image signal are transferred is the same. That is, when wired communication is established while the initialization data are transferred, the MPU 36c switches the communication with the head 20 from wireless communication to wired communication, determines to what point the initialization data have been transferred from the value of the internal counter, and transfers the rest of the initialization data via wired communication. Further, when wired communication is established while the image signal is transferred, the MPU 36c instructs the transfer control unit 26 to switch the communication with the head 20 from wireless communication to wired communication and transmit the image signal via wired communication.

(Case 2)

The case 2 will be described. As the situation that wired communication is established and then wireless communication is established, for example, it is conceivable that the endoscope apparatus 1 is activated in a state that the camera cable 50 is attached. Generally, wired communication is faster in communication speed than wireless communication, and thus it is conceivable that the wired communication is established first when the endoscope apparatus 1 is activated in a state that the camera cable 50 is attached.

When wired communication is established first in step S103 of FIG. 6, the communication establishment determining unit 38 outputs the "wired communication establishment signal". The MPU 36c determines that wired communication is established based on the "wired communication establishment signal" outputted from the communication establishment determining unit 38, and instructs the transfer control unit 26 to transmit the ID and the correction data via wired communication. When wireless communication is established while the ID and the correction data are transmitted via wired communication, the communication establishment determining unit 38 outputs the "wireless communication establishment signal".

The MPU 36c determines that wireless communication is established based on the "wireless communication establishment signal" outputted from the communication establishment determining unit 38. However, since the wired communication is faster in communication speed and higher in stability of communication than the wireless communication, the MPU 36c continues transmission of the correction data via wired communication without switching the communication.

Although the operation when the correction data are transferred has been described above, note that operation when the initialization data and the image signal are transferred is the same. That is, when wireless communication is established while the initialization data or image signal is transferred, the communication is not switched, and transfer of the rest of the initialization data or image signal is continued via wired communication without switching the communication.

(Case 3)

The case 3 will be described. As the situation that wired communication is established and then wireless communication is established, and thereafter the wired communication is disconnected, for example, it is conceivable that the endoscope apparatus 1 is activated in a state that the camera cable 50 is attached, and thereafter the camera cable 50 is removed.

When wired communication is established first in step S103 of FIG. 6, the communication establishment determining unit 38 outputs the "wired communication establishment signal". The MPU 36c determines that wired communication is established based on the "wired communication establishment signal" outputted from the communication establishment determining unit 38, and instructs the transfer control unit 26 to transmit the ID and the correction data via wired communication. When wireless communication is established while the ID and the correction data are transmitted via wired communication, the communication establishment determining unit 38 outputs the "wireless communication establishment signal".

The MPU 36c determines that wireless communication is established based on the "wireless communication establishment signal" outputted from the communication establishment determining unit 38. However, since the wired communication is faster in communication speed and higher in stability of communication than the wireless communication, the MPU 36c continues transfer of the rest of the correction data via wired communication without switching the communication.

Thereafter, when the camera cable 50 is removed while the correction data are transferred, the communication establishment determining unit 38 detects the disconnection of wired communication and outputs the "wired communication disconnection signal". The MPU 36c determines that the wired communication is disconnected based on the "wired communication disconnection signal" outputted from the communication establishment determining unit 38, and switches the communication with the head 20 from wired communication to wireless communication.

After the communication is switched, the MPU 36c instructs the transfer control unit 26 to transmit the ID via wireless communication. The MPU 36c determines whether the ID transmitted from the transfer control unit 26 and the ID obtained when the wired communication is established are the same or not. When the IDs are the same, the MPU 36c determines to what point the correction data have been transferred from the value of the internal counter, and instructs the transfer control unit 26 to transfer the rest of the correction data via wireless communication. Further, when the IDs are not the same, the MPU 36c resets the value of the internal counter, and instructs the transfer control unit 26 to transfer the correction data from the beginning.

Although the operation when the correction data are transferred has been described above, note that operation when the initialization data and the image signal are transferred is the same. That is, when wired communication is disconnected while the initialization data are transferred, the MPU 36c switches the communication with the head 20 from wired communication to wireless communication, determines to what point the initialization data have been transferred from the value of the internal counter, and transfers the rest of the initialization data via wireless communication. Further, when wired communication is disconnected while the image signal is transferred, the MPU 36c instructs the transfer control unit 26 to switch the communication with the head 20 from wired communication to wireless communication and transmit the image signal via wireless communication.

As has been described, since the endoscope apparatus 1 according to the first embodiment stores to what point the correction data and the initialization data are transferred by using the counter, it is unnecessary to start over the transfer of the correction data and the initialization data from the beginning when the communication state is switched from wireless communication to wired communication or switched from wired communication to wireless communication, allowing efficient transfer of data.

Further, the endoscope apparatus 1 according to the first embodiment uses wired communication in priority. Generally, wired communication has a fast transmission speed and high stability of communication compared to wireless communication. Thus, by using wired communication in priority, the communication speed and the stability can be secured.

Furthermore, since the state that wireless communication is established is maintained even when wired communication is established first, the communication can be switched immediately to the wireless communication to continue transfer of data when the wired communication is disconnected while the data are transmitted.

In addition, in the above description, although establishment of wired communication and wireless communication is started from the CCU 30 side, it may be structured such that establishment of wired communication and wireless communication is started from the head 20 side.

(Second Embodiment)

In a second embodiment, an embodiment will be described which transfers the correction data and the initialization data in different file formats via wired communication and wireless communication. Note that the same components as those of the endoscope apparatus 1 according to the first embodiment which are described with FIG. 1, FIG. 2, and FIG. 5 are denoted by the same numerals, and duplicated descriptions are omitted.

Figure 7:
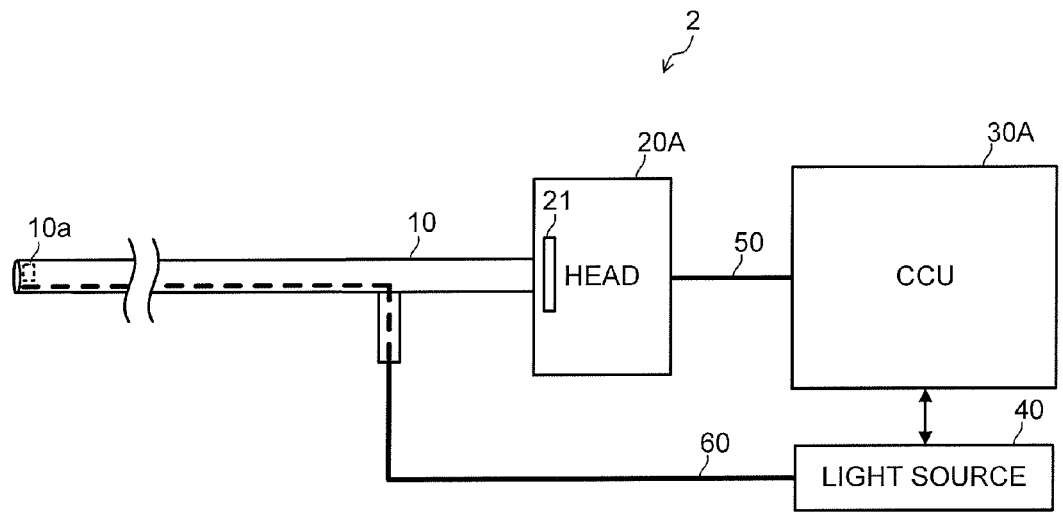
FIG. 7 is a structural diagram of an endoscope apparatus according to a second embodiment.

FIG. 7 is a structural diagram illustrating an endoscope apparatus 2 according to the second embodiment. As illustrated in FIG. 7, the endoscope apparatus 2 according to the second embodiment is different in structure from the endoscope apparatus 1 according to the first embodiment described with FIG. 1 in that it includes a head 20A and a CCU 30A.

Figure 8:
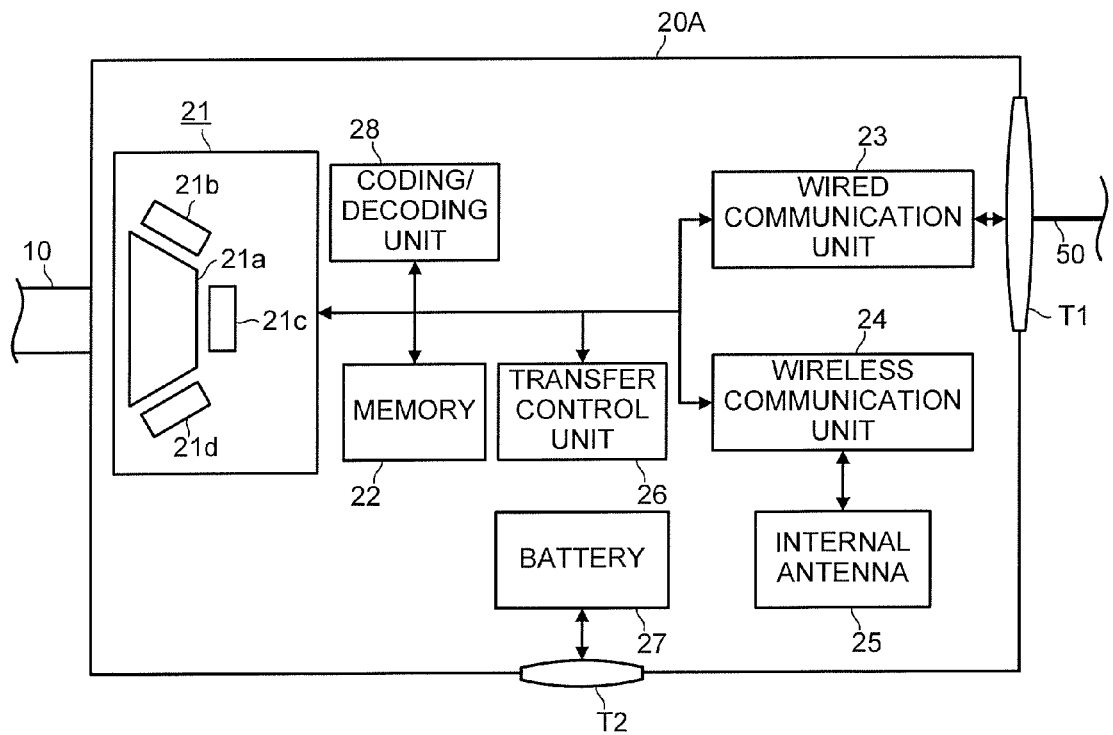
FIG. 8 is a structural diagram of a head.

FIG. 8 is a structural diagram of the head 20A provided in the endoscope apparatus 2 according to the second embodiment. As illustrated in FIG. 8, the head 20A of the endoscope apparatus 2 according to the second embodiment is different from the head 20 of the endoscope apparatus 1 according to the first embodiment in that it includes a coding/decoding unit 28.

The coding/decoding unit 28 of the head 20A lossless compresses the correction data and data of the image signal to be transferred from the memory 22 to the CCU 30A based on an instruction from the transfer control unit 26. Further, the coding/decoding unit 28 decodes the initialization data transferred from the CCU 30A to the memory 22 based on an instruction from the transfer control unit 26.

Specifically, when the correction data and data of the image signal are transferred to the CCU 30A using wireless communication, the transfer control unit 26 instructs the coding/decoding unit 28 to lossless compress (code) the correction data and data of the image signal to be transferred to the CCU 30A, and the transfer control unit 26 transfers the correction data and data of the image signal which are lossless compressed in the coding/decoding unit 28 to the head 20A. Further, when the initialization data are transmitted from the CCU 30A using wireless communication, the transfer control unit 26 instructs the coding/decoding unit 28 to decode the lossless compressed initialization data to return them to the data before being compressed, and stores the decoded initialization data in the memory 22.

Figure 9:
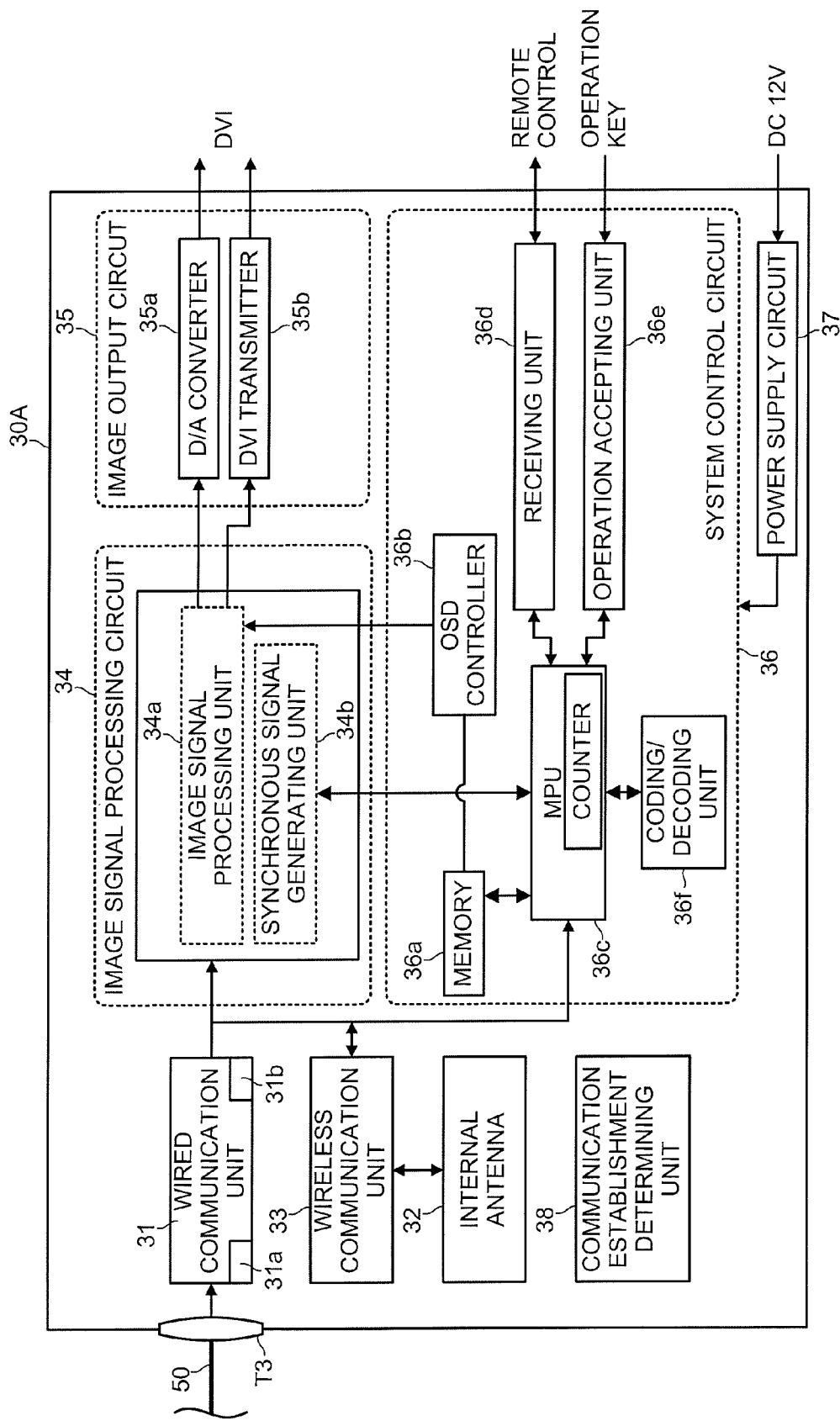
FIG. 9 is a structural diagram of a CCU.

FIG. 9 is a structural diagram of the CCU 30A provided in the endoscope apparatus 2 according to the second embodiment. As illustrated in FIG. 9, the CCU is different from the CCU 30 of the endoscope apparatus 1 according to the first embodiment in that a system control circuit 36A provided in the CCU 30A of the endoscope apparatus 2 according to the second embodiment includes a coding/decoding unit 36f.

The coding/decoding unit 36f of the CCU 30A lossless compresses the initialization data to be transferred from the memory 36a to the head 20A based on an instruction from the MPU 36c. Further, the coding/decoding unit 36f decodes the lossless compressed correction data and data of the image signal transferred from the head 20A based on an instruction from the MPU 36c.

Specifically, when transmitting the initialization data to the head 20A using wireless communication, the MPU 36c instructs the coding/decoding unit 36f to lossless compress the initialization data to be transmitted, and transmits the initialization data lossless compressed in the coding/decoding unit 36f to the head 20. Further, when the correction data and data of the image signal are transmitted to the CCU 30A using wireless communication, the MPU instructs the coding/decoding unit 36f to decode the correction data and data of the image signal to return them to the data before being compressed, and stores the decoded correction data and data of the image signal in a memory 236a.

As described above, when data (correction data, initialization data, and image signal data) are transferred via wireless communication, the endoscope apparatus 2 according to the second embodiment transfers lossless compressed data. Generally, wireless communication has a slow communication speed compared to wired communication, but while performing wireless communication, the volume of data is reduced by lossless compressing the data to be transferred, and thus the time taken for data transfer can be shortened.

(Third Embodiment)

Figure 10:
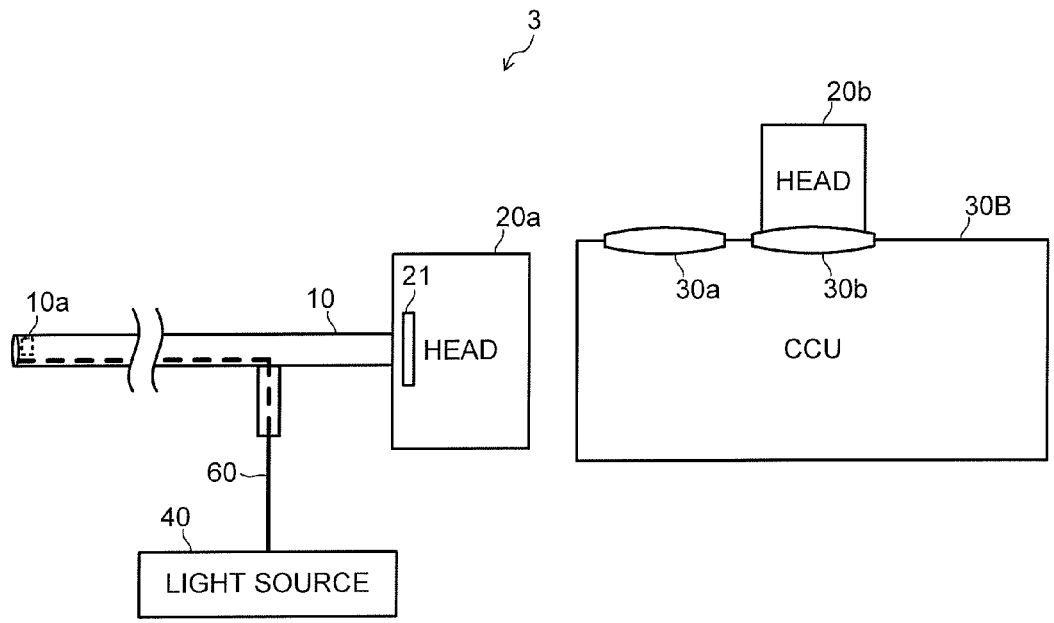
FIG. 10 is a structural diagram of an endoscope apparatus according to a third embodiment.

FIG. 10 is a structural diagram of an endoscope apparatus 3 according to a third embodiment. Hereinafter, the endoscope apparatus 3 according to the third embodiment will be described. The same components as those of the endoscope apparatus 1 according to the first embodiment which are described with FIG. 1, FIG. 2, and FIG. 5 are denoted by the same numerals, and duplicated descriptions are omitted.

The endoscope apparatus 3 according to the third embodiment includes a plurality of heads 20a, 20b, and a CCU 30B used in common between the heads 20a, 20b. The CCU 30B includes a plurality of terminals 30a, 30b for charging batteries provided in the heads 20a, 20b, and performs transfer of the correction data and the initialization data while the batteries of the heads 20a, 20b connected to the terminals 30a, 30b are charged.

Here, in the third embodiment, the head in use (head 20a in FIG. 10) communicates with the CCU 30B via wireless communication, and the other head (head 20b in FIG. 10) is connected to one of the terminals 30a, 30b of the CCU 30B to have the battery charged.

Figure 11:
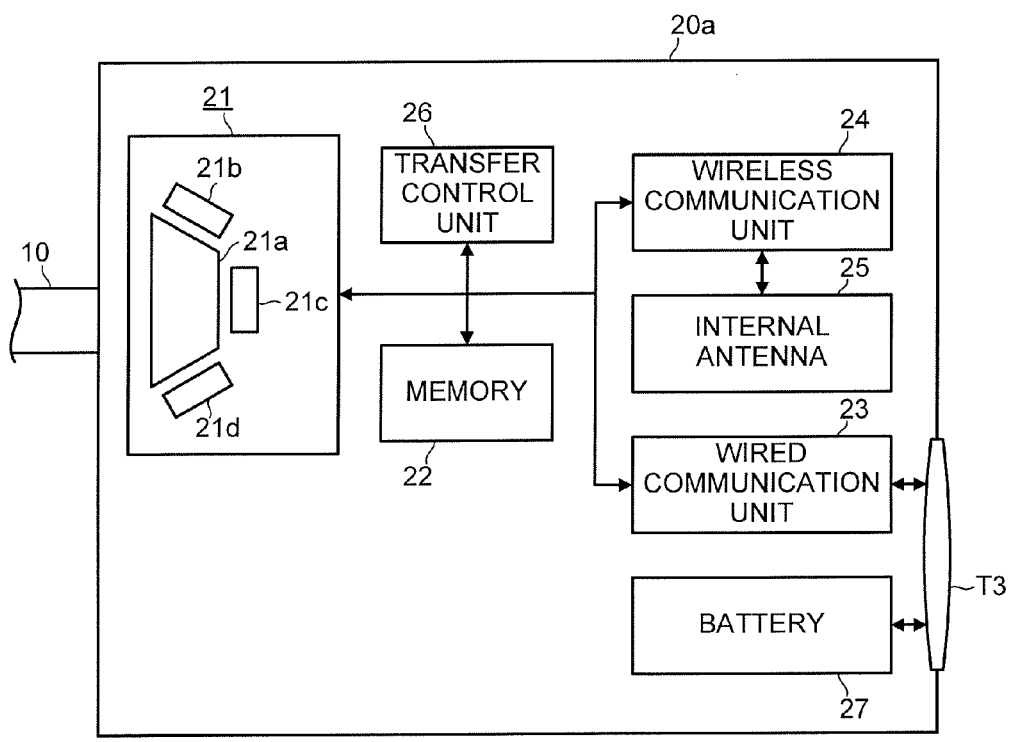
FIG. 11 is a structural diagram of a head.

FIG. 11 is a structural diagram of the head 20a. Note that the heads 20a, 20b have the same structure, and thus only the head 20a will be described here. As illustrated in FIG. 11, the head 20a of the endoscope apparatus 3 according to the third embodiment is different from the head 20 of the endoscope apparatus 1 according to the first embodiment described with FIG. 2 in that it includes a terminal T3 combining a connection terminal for the wired communication unit 23 and a charging terminal for the battery 27. By connecting this terminal T3 to one of the terminals 30a, 30b of the CCU 30B, it becomes possible to perform wired communication with the CCU 30B and to charge the battery 27. In addition, IDs (identifiers) different from each other are stored in the memories 22 of the heads 20a, 20b, respectively.

Further, the connection terminal for the wired communication unit 23 and the charging terminal for the battery 27 need not necessarily be combined, and can be structured of separate terminals as long as they have shapes such that contacts with both the terminals are made when the head is brought into contact with the CCU 30B.

Figure 12:
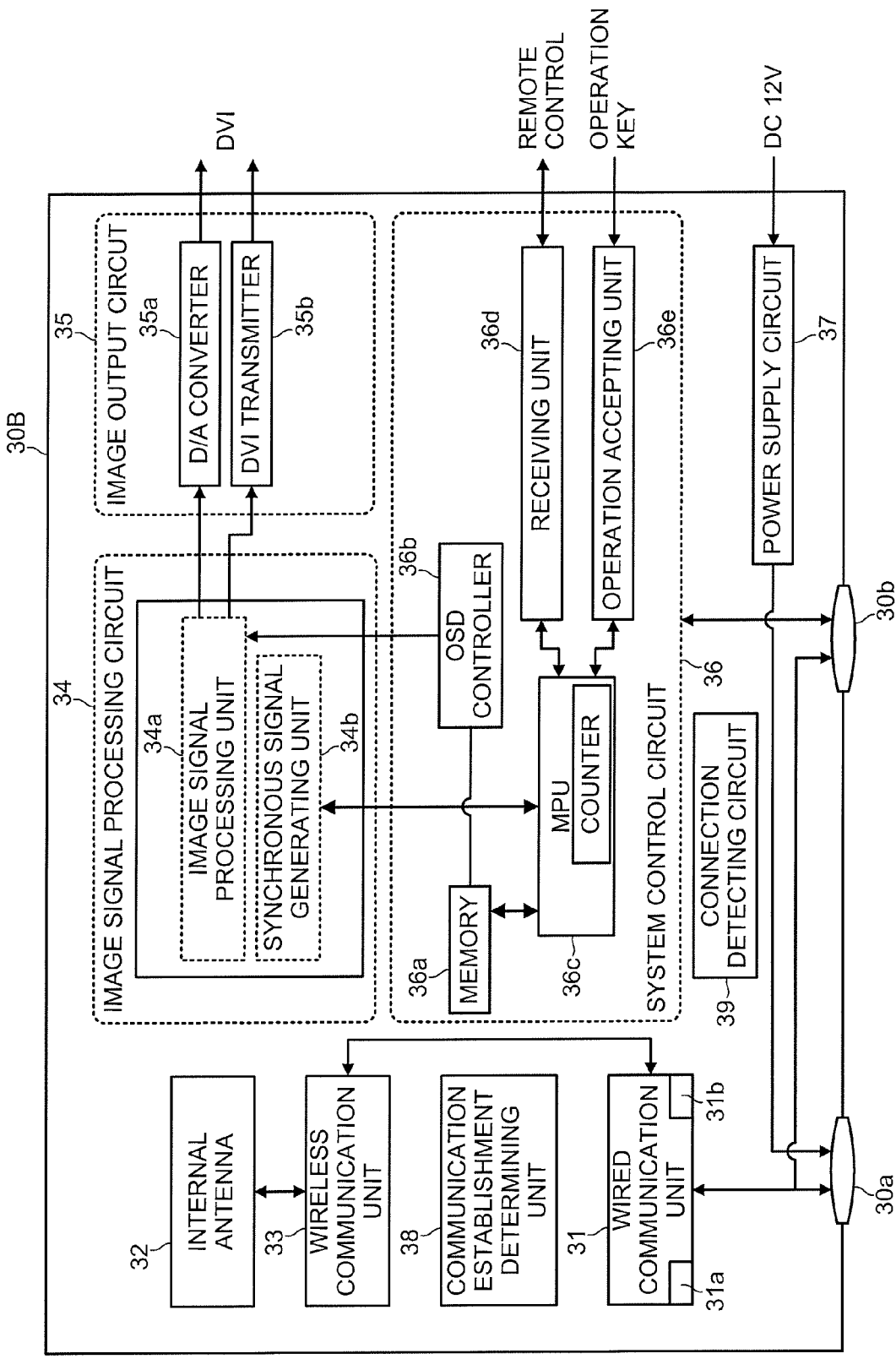
FIG. 12 is a structural diagram of a CCU.

FIG. 12 is a structural diagram of the CCU 30B. As illustrated in FIG. 12, the CCU 30B includes the plurality of terminals 30a, 30b and a connection detecting circuit 39. Each of the terminals 30a, 30b is a terminal combining a connection terminal for the wired communication unit 31 and a charging terminal for the battery 27 provided in the head 20*a*, 20*b*. Each of the terminals 30*a*, 30*b* is connected to the wired communication unit 31 and the power supply circuit 37, and when the terminal T3 of the head 20*a*, 20*b* is connected thereto, it becomes possible to perform wired communication with the head 20*a*, 20*b* and charge the battery 27 of the head 20*a*, 20*b*.

The connection detecting circuit 39 detects connection of the head 20*a*, 20*b* to the terminal 30*a*, 30*b*. When the terminal T3 of the head 20*a*, 20*b* is connected to the terminal 30*a*, 30*b*, the connection detecting circuit 39 notifies the MPU 36*c* and the power supply circuit 37 of the terminal to which the head 20*a*, 20*b* is connected.

Figure 13:
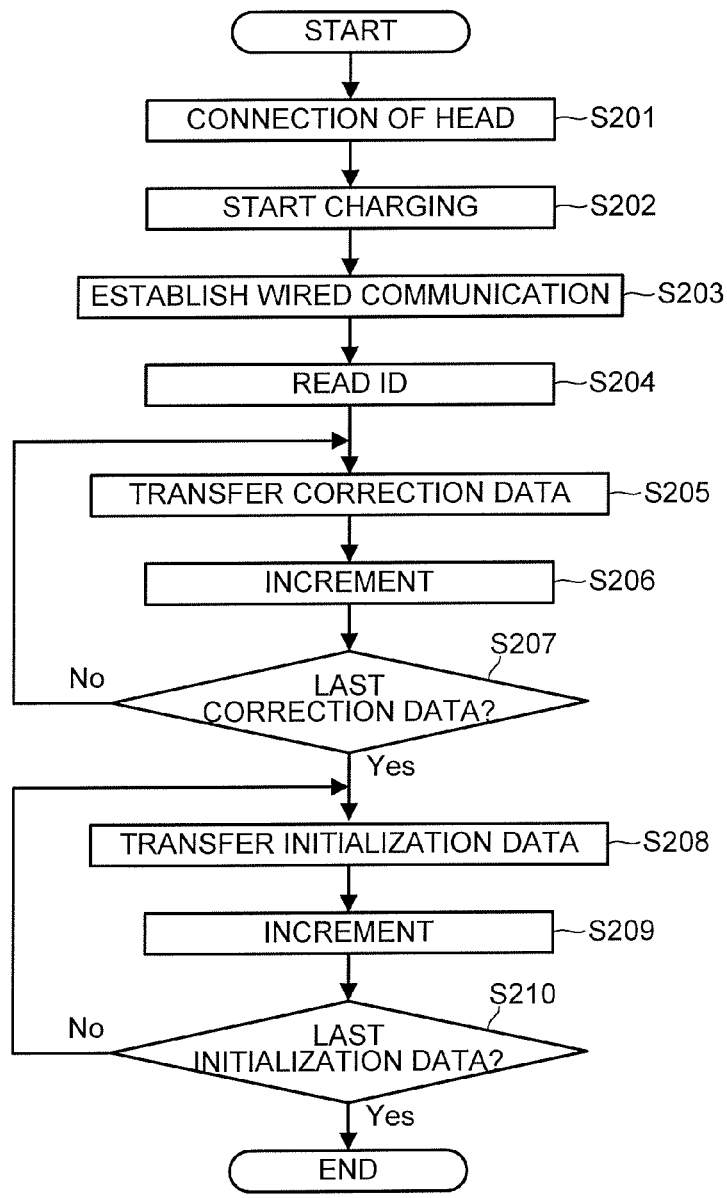
FIG. 13 is a flowchart illustrating operation of the endoscope apparatus.

Next, operation while the head 20*a*, 20*b* provided in the endoscope apparatus 3 according to the third embodiment is charged will be described. FIG. 13 is a flowchart illustrating the operation of the endoscope apparatus 3 according to the third embodiment. Note that in the following, operation in the case where the head 20*a* is in use and the head 20*b* is connected to the terminal 30*b* of the CCU 30B will be described.
(Step S201)

When the terminal T3 of the head 20*b* is connected to the terminal 30*b* provided in the CCU 30B, the connection detecting circuit 39 detects that one of the head 20*a* and the head 20*b* is connected to the terminal 30*b*. The connection detecting circuit 39 notifies the MPU 36*c* and the power supply circuit 37 of the connection of the head to the terminal 30*b*.
(Step S202)

Based on the notification from the connection detecting circuit 39, the power supply circuit 37 supplies power to the terminal 30*b* which is notified, thereby starting charging of the battery 27 of the head 20*b*.
(Step S203)

The MPU 36*c* instructs the wired communication unit 31 to establish wired communication with the head 20*b* based on the notification from the connection detecting circuit 39. The wired communication unit 31 establishes wired communication with the wired communication unit 23 of the head 20*b* via the terminal 30*b* based on the instruction from the MPU 36*c*.
(Step S204)

Once the wired communication is established, the MPU 36*c* instructs the transfer control unit 26 to transmit the ID from the memory 22 of the head 20*b*, and stores the transmitted ID in the memory 36*a*.
(Step S205)

Once the ID is stored, the MPU 36*c* instructs the transfer control unit 26 to transmit the correction data from the memory 22 of the head 20*b*, and stores the transmitted correction data in the memory 36*a* in association with the ID which is read in advance.
(Step S206)

First, the MPU 36*c* instructs the transfer control unit 26 to transmit the number of correction data, and stores the transmitted correction data number in the memory 36*a*. Next, the MPU 36*c* instructs the transfer control unit 26 to sequentially transmit the correction data stored in the memory 22, and stores the transmitted correction data in the memory 36*a*. At this time, the MPU 36*c* increments the value of the internal counter every time a piece of the correction data is stored in the memory 36*a*.
(Step S207)

The MPU 36*c* determines whether the piece of the correction data stored in the memory 36*a* in step S106 is the last piece of the correction data or not. Specifically, the MPU 36*c* determines whether or not the value of the internal counter is equal to the correction data number stored in the memory 36*a*.

When the value of the internal counter is not equal to the correction data number stored in the memory 36*a* (No in step S207), the MPU 36*c* repeats the operation of step S205 to step S207 until the value of the internal counter becomes equal to the correction data number stored in the memory 36*a*.
(Step S208)

When the value of the internal counter is equal to the correction data number stored in the memory 36*a* (Yes in step S207), the MPU 36*c* reads out the initialization data (for example, resolution, clock, mode, and so on) from the memory 36*a* and transmits the read data to the head 20. The initialization data transmitted to the head 20 are stored in the memory 22 by the transfer control unit 26.
(Step S209)

The MPU 36*c* increments the value of the internal counter every time a piece of the initialization data is transferred.
(Step S210)

The MPU 36*c* determines whether the piece of the initialization data transferred in the step S208 is the last piece of the initialization data or not. Specifically, the MPU 36*c* determines whether or not the value of the internal counter is equal to the initialization data number stored in the memory 36*a*.

When the value of the internal counter is not equal to the initialization data number stored in the memory 36*a* (No in Step S210), the MPU 36*c* repeats the operation of step S208 to step S210 until the value of the internal counter becomes equal to the correction data number stored in the memory 36*a*.

When the value of the internal counter is equal to the initialization data number stored in the memory 36*a* (Yes in Step S110), the MPU 36*c* finishes the transfer of initialization data.

As described above, the endoscope apparatus 3 according to the third embodiment includes the plurality of heads 20*a*, 20*b*, and the CCU 30B used in common between the heads 20*a*, 20*b*, and performs transfer of the correction data and the initialization data while the batteries in the head 20*a*, 20*b* connected to the terminals 30*a*, 30*b* of the CCU 30 are charged. Thus, it is unnecessary to transfer the correction data and the initialization data via wireless communication, which has slow communication speed compared to wired communication, when the heads 20*a*, 20*b* are used, and the image signal transferred from the heads 20*a*, 20*b* can be corrected immediately to obtain a clear image. Accordingly, convenience for the user improves.

In the imaging apparatus or the endoscope apparatus according to at least one of the above-described embodiments, a main unit (CCU) includes a first communication unit (wireless communication unit) transmitting/receiving data to/from the head unit via wireless communication, a second communication unit (wired communication unit) transmitting/receiving data to/from the head unit via wired communication, and a control unit (MPU) detecting whether the second communication unit is communicable, and continuing, when the first and second communication units are switched based on a detection result therefrom, transmission/reception of the data which is performed before the switching. Thus, even when the communication state changes, transfer of data can be performed continuing from the data which have been transferred.

While certain embodiments have been described, these embodiments have been presented by way of example only, and are not intended to limit the scope of the inventions. Indeed, the novel embodiments described herein may be embodiment in a variety of other forms; furthermore, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A head separated type imaging apparatus comprising:
a plurality of head units; and
a main unit separate from the plurality of head units, the main unit processing an image signal transmitted from a head unit of the plurality of head units,
wherein each of the plurality of head units stores a unique identifier and correction data of the image signal;
wherein the main unit comprises:
a first communication unit receiving the correction data from the plurality of head units via wireless communication;
a second communication unit receiving the correction data from the plurality of head units via wired communication; and
a control unit detecting whether the first communication unit and the second communication unit are communicable, obtaining the identifier and the correction data by the second communication unit in priority when the first communication unit and the second communication unit are communicable, obtaining the identifier again when switching the first communication unit and the second communication unit, and when the identifier received just before the communication switching is the same as the identifier received just after the communication switching, continuing reception of the rest of the correction data from the point of communication switching;
wherein the control unit determines the communication switching point of the correction data transfer from a value of a counter that is counting a number of the correction data transferred by the first communication unit or the second communication unit, and instructs the head unit to transfer the rest of the correction data, and
wherein the first communication unit is communicable with the plurality of head units when reception of the correction data is performed by the second communication unit.

2. The apparatus of claim 1,
wherein the control unit switches form the first communication unit to the second communication unit and continues reception of the correction data when the second communication unit becomes communicable after the first communication unit becomes communicable, and
does not switch to the first communication unit and maintains the reception of the correction data when the first communication unit becomes communicable after the second communication unit becomes communicable.

3. The apparatus of claim 1, further comprising;
the counter counting the number of the correction data transmitted by the first communication unit or the second communication unit; and
wherein the control unit continues the reception of the correction data based on the number counted by the counter.

4. The apparatus of claim 1,
wherein the main unit further comprises a first compression unit compressing the data to be transmitted to at least one head unit of the plurality of head units; and
wherein the first compression unit compresses the data to be transmitted to the at least one head unit based on a detection result in the control unit.

5. The apparatus of claim 1,
wherein the head unit further comprises a second compression unit compressing the data; and
wherein the second compression unit compresses the data to be transmitted to the main unit based on a detection result in the control unit.

6. An activating method of a head separated type imaging apparatus that comprises a plurality of head units and a main unit, the main unit includes a first communication unit to receive correction data of image signal via wireless communication with the plurality of head units storing a unique identifier and correction data of the image signal, a second communication unit to receive correction data of image signal via wired communication with the plurality of head units, and a control unit switching between the first communication unit and the second communication unit, the method comprising:
storing, by the control unit, a unique identifier and correction data of the image signal from each of the plurality of head units;
detecting, by the control unit, whether the first communication unit and the second communication unit are communicable;
obtaining the identifier and the correction data by using the second communication unit in priority when the first communication unit and the second communication unit are communicable;
obtaining the identifier again when switching the first communication unit and the second communication unit; and
when the identifier received just before the communication switching is the same as the identifier received just after the communication switching, continuing the reception of the rest of the correction data from the point of communication switching;
wherein the control unit determines the communication switching point of the correction data transfer from a value of a counter that is counting a number of the correction data transferred by the first communication unit or the second communication unit, and instructs the head unit to transfer the rest of the correction data, and
wherein the first communication unit is communicable with the plurality of head units when reception of the correction data is performed by the second communication unit.

7. The method of claim 6,
wherein the control unit switches from the first communication unit to the second communication unit and continues reception of the correction data when the second communication unit becomes communicable after the first communication unit becomes communicable, and
does not switch to the first communication unit and maintain the reception of the correction data when the first communication unit becomes communicable after the second communication unit becomes communicable.

8. The method of claim 6, further comprising;
the counter counting the number of the correction data transmitted by the first communication unit or the second communication unit, and
wherein the control unit continues the reception of the correction data based on the number counted by counter.

9. The method of claim 6,
wherein the main unit further comprises a first compression unit compressing the data to be transmitted to at least one head unit of the plurality of head units; and
wherein the first compression unit compresses data to be transmitted to the at least one head unit of the plurality of head units based on a detection result in the control unit.

10. The method of claim 6,
wherein each of the plurality of head units further comprises a second compression unit compressing the correction data; and
wherein the second compression unit compresses the correction data to be transmitted to the main unit based on a detection result in the control unit.

11. A head separated type endoscope apparatus comprising:
a plurality of head units including a scope to be inserted into a subject to be inspected and imaging an inside of the subject to be inspected; and
a main unit separate from the plurality of head units, the main unit processing an image signal transmitted from a head unit of the plurality of head units,
wherein each of the plurality of head units stores a unique identifier and correction data of the image signal;
wherein the main unit comprises:
a first communication unit receiving the correction data from the plurality of head units via wireless communication;
a second communication unit receiving the correction data from the plurality of head units via wired communication; and
a control unit detecting whether the first communication unit and the second communication unit are communicable, obtaining the identifier and the correction data by using the second communication unit in priority when the first communication unit and the second communication unit are communicable, obtaining the identifier again when switching the first communication unit and the second communication unit, and when the identifier received just before the communication switching is the same as the identifier received just after the communication switching, continuing reception of the rest of the correction data from the point of communication switching;
wherein the control unit determines the communication switching point of the correction data transfer from a value of a counter that is counting a number of the correction data transferred by the first communication unit or the second communication unit, and instructs the head unit to transfer the rest of the correction data, and
wherein the first communication unit is configured to communicate with the plurality of head units when reception of the correction data is performed by the second communication unit.

12. The apparatus of claim 11,
wherein the control unit switches from the first communication unit to the second communication unit and continues the reception of the correction data when the second communication unit becomes communicable after the first communication unit becomes communicable, and
does not switch to the first communication unit and maintains the reception of the correction data when the first communication unit becomes communicable after the second communication unit becomes communicable.

13. The apparatus of claim 11, further comprising;
the counter counting the number of the correction data transmitted by the first communication unit or the second communication unit, and
wherein the control unit continues the reception of the correction data based on the number counted by the counter.

14. The apparatus of claim 11,
wherein the main unit further comprises a first compression unit compressing data to be transmitted to the head unit; and
wherein the first compression unit compresses the data to be transmitted to the head unit based on a detection result in the control unit.

15. The apparatus of claim 12,
wherein the head unit further comprises a second compression unit compressing the correction data; and
wherein the second compression unit compresses the correction data to be transmitted to the main unit based on a detection result in the control unit.

16. The apparatus of claim 1, wherein the data includes the correction data.

17. The apparatus of claim 4, wherein the data includes initialization data.

18. The apparatus of claim 17, wherein the initialization data comprises at least one of resolution and clock information.

* * * * *